United States Patent [19]

Hell et al.

[11] 4,019,958

[45] Apr. 26, 1977

[54] CONTINUOUS PROCESS OF PRODUCING PANCREATIN AND PRODUCT THEREOF

[75] Inventors: Hans Hell, Neustadt am Rubenberg; Günter Peschke, Hannover; Horst Oppermann; Rudolf Kaufung, both of Neustadt am Rubenberg; Siegfried Funke, Hannover; Werner Stühmer, Springe, all of Germany

[73] Assignee: Kali-Chemie Pharma GmbH, Hannover, Germany

[22] Filed: Mar. 19, 1976

[21] Appl. No.: 668,524

[30] Foreign Application Priority Data

Mar. 22, 1975 Germany .......................... 2512746

[52] U.S. Cl. ................................. 195/62; 195/66 R
[51] Int. Cl.² ....................................... C07G 7/026
[58] Field of Search ............................ 195/66 R, 62

[56] References Cited

UNITED STATES PATENTS 3,844,891 10/1974 Hess et al. ................... 195/66 R X

FOREIGN PATENTS OR APPLICATIONS 1,328,202 8/1973 United Kingdom ............. 195/66 R

*Primary Examiner*—Lionel M. Shapiro
*Attorney, Agent, or Firm*—Bacon & Thomas

[57] ABSTRACT

A freely flowable pancreatin of high amylolytic, lipolytic, and proteolytic activity, of a low germ content and substantially free of pathogenic germs and fibrous tissue material, of a high bulk weight between about 500 g./liter and about 700 g./liter and a very fine particulate size is produced according to the continuous process of extracting finely comminuted pancreas glands with a mixture of chlorinated hydrocarbons and fluoro-chloro-carbons and, if required, water, separating the fat-containing solvent phase, and recovering pancreatin from the enzyme phase.

13 Claims, No Drawings

CONTINUOUS PROCESS OF PRODUCING PANCREATIN AND PRODUCT THEREOF

BACKGROUND OF THE INVENTION

1. Field of the Invention

The present invention relates to an advantageous and novel process of producing pancreatin of a high amylolytic, lipolytic, and proteolytic activity, and more particularly to such a continuous process of producing pancreatin while at the same time considerably reducing the bacterial count and completely eliminating the undesirable germs therein, and to a pancreatin preparation which is substantially free of germs as they are to be excluded in accordance with the provisions of the U.S. Pharmacopeia XVIIIth Revision.

2. Description of the Prior Art

Deep-frozen pancreas glands are usually employed as starting materials for producing pancreatin because only frozen materials can be stored without considerable losses of enzyme activity for a prolonged period of time. The preferred starting materials are the pancreas glands of hogs due to their high content of amylolytic and lipolytic activities.

A number of different processes for producing pancreatin are described in the literature. Thus, an extract in which the pro-enzymes of the proteases are activated by the addition of trypsin or enterokinase is produced, for instance, by treating and extracting the comminuted, frozen, or thawed glands with water, salt solutions, or solvents, such a dilute glycerin, 25% ethanol, 20% acetic acid. Such an extract is subjected subsequently to precipitation with inorganic salts, organic solvents, or tannin and is then converted by careful drying into a powder.

Pancreatin can also be produced by removing the water at a low temperature from the comminuted gland material, for instance, by freeze-drying, vacuum drying or azeotropic distillation, with subsequent removal of fat by extraction with organic solvents or by simultaneous dehydration and defattening, for instance, by means of acetone, alcohols, or, alternatively, by mixtures of acetone and an ether, followed by drying.

According to British Pat. No. 822,741 of Oct. 28, 1959 and French Pat. No. 1,295,302 of July 8, 1962, pancreas glands are first subjected to a mechanical fat removal treatment, are comminuted to a particle size of 1 mm. to 2 mm., are further subjected in a container to fat extraction by means of diethyl ether in batch procedure, and are subsequently converted by centrifuging into three phases, namely, an ether-fat phase, the pancreas juice-phase, and the meat residue. Pancreatin products of therapeutic value are precipitated from the pancreas juice by the addition of ammonium sulfate.

At the present time hog pancreas glands to be used as starting material for the production of pancreatin are collected exclusively on a large scale from slaughterhouses and meat packaging plants. When removing the pancreas glands from the gastric-intestinal bundles of freshly slaughtered animals, contamination cannot be prevented under normal slaughterhouse conditions. Therefore, germ counts, i.e. the number of pathogenic plus apathogenic germs present in each gram of material, have been found to amount to $10^4$/g. to $10^8$/g. found on examination of glands collected under such conditions.

Microbially-pure drugs are generally subdivided into three groups, namely into sterile preparations, into preparations free of pathogenic germs, and into preparations which are of a low germ content. Such preparations have been produced by the pharmaceutical industry for some time in the form of injectable, dermatological and ophthalmological preparations, and in the form of preparations applicable to the mucous membranes. Recently, however, more and more attempts have been made to also produce orally administrable preparations of a substantial microbial purity. But meeting this requirement is quite difficult when producing biological preparations derived from animal organs.

Pancreatin, as a natural biological product with its highly sensitive enzyme components, is contaminated with respect to type and count of germs to a varying extent and frequently is not free of pathogenic germs.

Attempts have already been made to reduce the bacterial count or germ number in pancreatin preparations. Thus, for instance, B. Schlatter treats pancreatin with isopropanol and water or with γ-rays or with both simultaneously as described in his dissertation deposited at the Technical University of the Swiss Federation at Zuerich 1971; and in Pharm. Acta Helvetiae Vol. 49, page 41 (1974). The mixture of solvents is removed by azeotropic distillation after the isopropanol-water treatment.

A treatment of pancreatin with γ-rays in order to reduce the germ count has also been described in Czechoslovakain Pat. No. 147,274.

Experiments to reduce the bacterial count or germ number by a treatment with ethylene oxide have furthermore been carried out by A. Libicky et al. as described in "Die Pharmazie" vol. 22 (1967), page 311, and vol. 23 (1968), page 21.

Reduction of the germ content in pancreatin is effected in the manner described in German Offenlegungsschrift No. 2,135,025. Said process consists in treating pancreatin with halogenated hydrocarbons of a boiling point between 15° and 100° C. or, respectively, with aliphatic ketones in the presence of water and cellulose derivatives. Halogenated hydrocarbons which are suitable for this treatment are exclusively chlorinated hydrocarbons, namely methylene chloride and chloroform. 100 g. of the resulting pourable pancreatin granulate are free of Salmonella germs and 1 g. thereof is free of Enterobacteria and Pseudomonas bacteria and the total bacterial count or germ number therein is lower than $10^4$.

According to the process described in German Offenlegungsschrift No. 2,106,706 pancreatin is mixed with calcium compounds and the mixture is heated at 82° C. under atmospheric pressure for several hours in order to destroy Salmonella bacteria.

While pancreatin is used as a starting material in the above-mentioned processes for reducing the germ number, there has become known also a process for destroying Salmonella bacteria when using pancreas glands as starting material. See E. J. G. Glencross in Brit. Med. Journal vol. 2, page 376 (1972). According to said process, the pancreas glands are treated with an aqueous solution of hypochlorite, are comminuted, ground, dried in a vacuum, and subjected to a defattening process.

All the above-described processes for reducing the germ number or bacterial count of pancreatin preparations are very complicated and, in addition thereto, are accompanied by considerable losses in activity.

SUMMARY OF THE INVENTION

It is one object of the present invention to provide a simple and effective continuous process of producing pancreatin of a high amylolytic, lipolytic, and proteolytic activity which has a low germ content and is substantially free of fibrous tissue material.

Another object of the present invention is to provide a pancreatin preparation of considerably reduced bacterial count or germ number, which is substantially free of all germs which are undesirable according to the specifications of the U.S. Pharmacopeia XVIIIth Revision and also of fibrous tissue material and which has a high bulk weight or apparent density.

Other objects of the present invention and advantageous features thereof will become apparent as the description proceeds.

In principle, the process according to the present invention comprises the following steps carried out in continuous operation:

a. Frozen, finely comminuted pancreas glands are continuously subjected, if desired after addition of water, to the action of a mixture of liquid chlorinated hydrocarbons and liquid fluoro-chloro-carbons for a short period of time in order to remove the fat and to decrease the germ content;

b. Separating the solvent phase containing the fat; and c. Concentrating and drying the enzyme phase.

When carrying out this process, it is quite surprising that during the fat removal step, the germ number or bacterial count is considerably reduced while at the same time all those germs are destroyed which, according to the specifications of U.S. Pharmacopeia XVIIIth revision, are undesired. The resulting final product is a pancreatin of a high bulk weight which is substantially free of fibrous tissue material.

The continuous process according to the present invention furthermore permits the glands to be subjected under the most gentle conditions to a very short period of processing time.

The resulting final product is of light color. It can readily be processed to galenical preparations due to its fluid and readily flowable property. It is distinguished over known preparations by its high enzymatic activity. Said high activity is due, on the one hand, to the novel mode of continuously processing the glands and, on the other hand, to the presence of fluoro-chloro-carbons during the fat removal step.

According to the present invention the gland material is very finely ground until the cells are completely disintegrated and their cellular structure is destroyed. As a result thereof, highly effective fat extraction within a short period of time is achieved by the treatment with the mixture of chlorinated hydrocarbons and fluoro-chloro-carbons. Furthermore, such very fine comminution yields a practically fiber-free material so that subsequent additional grinding and comminution of the resulting pancreatin, which has always heretofore caused loss in enzymatic activity, is not necessary. It is, of course, of importance with respect to the grinding process that the temperature of the gland material is kept as low as possible.

Water may be added to the comminuted starting material, if desired, together with the mixture of the halogenated solvents. The proportion by weight of pancreas glands with respect to water can vary quite considerably. It may be between about 1:0 and about 1:10.

Removal of fat combined with the reduction in germ content is carried out at a somewhat increased temperature, i.e., at a temperature between about 30° and about 60° C. within a short period of time. Under such conditions no noticeable destruction of the enzymes takes place. Countercurrent extraction in centrifugal extracting devices is effected, in general, between about 30 seconds and about 5 minutes, whereby the temperature should not exceed 60° C. In accordance with the present invention, mixtures of chlorinated hydrocarbons and fluoro-chloro-carbons are employed in this process step. The use of such mixtures not only results in a satisfactory removal of fat and in a sufficient reduction of germs, but also prevents losses in enzyme activity in spite of the increased extraction temperature. The proportion, by weight, of pancreas glands to halogenated hydrocarbons can also vary within wide limits. It may be between about 1:2 and about 1:50.

Solvents which are useful in the process according to the present invention are chlorinated hydrocarbons, the boiling point of which is between about 20° and about 150° C., preferably dichloromethane, trichloro methane, dichloroethane, trichloroethane and tetrachloroethane. The fluoro-chloro-carbons preferably have a boiling point between about 20° and about 150° C. Especially useful extraction solvents are trichloro fluoro methane, trichloro trifluoro ethane, tetrachloro difluoroethane and pentachloro monofluoro ethane. The chlorinated hydrocarbons and the fluoro-chloro-carbons are preferably used in a proportion, by weight, between about 1:0.05 and about 1:2.

Concentration of the enzyme phase is carried out in a vacuum at a low temperature. Preferably concentration is effected in short time evaporators, i.e. high speed evaporators, wherein the enzyme phase remains at the most for five seconds, while the temperature of the product does not substantially exceed 60° C. If these durations and temperatures are exceeded, losses in activity are encountered.

The pancreatin is dried under very gentle conditions. For this purpose, well known drying processes such as freeze-drying, vacuum-drying, spray-drying can be used.

A further advantage of the process according to the present invention is the fact that the pancreatin, after it has been dried gently, is obtained as a product of a relatively high bulk weight, namely of a bulk weight between about 500 g. per liter and about 700 g. per liter and in the form of very finely divided particles, i.e. of particles of a mean particle diameter between about 30 $\mu$m. and about 50 $\mu$m. The combination of these two properties enables a high dosage at small volumes during the therapeutic utilization of the pancreatin. Concommitantly, as a consequence of the fineness of particle size, there results an accelerated release of the enzyme in the digestive tract.

When processing pancreas glands in the manner heretofore used, there are obtained, in general, products with a considerably lower bulk weight of about 300 g. per liter to 400 g. per liter. A further increase of said bulk weight is possible only by subjecting the products to an additional granulation or densifying process. It is also possible to obtain a higher bulk density by precipitation of the pancreatin out of extracts by means of salts, however, then the high bulk density is conditional upon contamination if the pancreatin with the precipitation agent.

The product prepared in accordance with the process of the invention is characterized by being free of fibrous material, whereas the fiber content of prior art products is often very large. A product which is not fiberfree is encumbered by inert ballast substance, so that the end product possesses a lower enzymatic activity per unit weight. Moreover, the enzymes are released more slowly from such products. The preparation of tablets and dragees is made more difficult by the presence of fibers, and in addition, such dosage forms have a tendency toward cracking as a result of the presence of these fibers.

When proceeding according to the present invention, the product is kept in a well flowable state starting with the comminution step up to the drying step. The product is to be cooled very rapidly to temperatures at which no destruction of the enzymes can take place each time it has been subjected to process steps in which increased temperatures were employed. The most favorable temperature range after cooling is between about 0° C. and about 8° C.

The process according to the present invention has the further advantage that the entire equipment following the defattening step in which the germ count is reduced, is protected against microbial contamination.

A particular advantage of the process according to the present invention is the feature that, when processing the pancreas glands, defattening and reduction of the germ count take place simultaneously in one step of operation without having to make allowance for losses in enzyme activity. Heretofore no process for producing pancreatin has become known in which the total germ count is reduced and in which the germs which are undesirable according to the specifications of U.S. Pharmacopeia XVIIIth Revision are completely eliminated. The only heretofore known process, in which the starting material for producing pancreatin, namely the pancreas glands, are treated with a hypochlorite solution in order to destroy the Salmonella bacteria, has the disadvantage that considerable losses in enzyme activity are encountered thereby.

DESCRIPTION OF THE PREFERRED EMBODIMENTS

The following examples serve to illustrate the present invention without, however, limiting the same thereto.

EXAMPLE 1

25 kg./hour of deep-frozen pancreas glands (frozen at a temperature of −20° C.) are finely comminuted in a continuously operating milling equipment in several grinding steps. The resulting paste of a temperature of 0° C. is mixed with 6 kg./hour of water at 20° C. in a continuous-flow mixing device. The fat is extracted from said mixture in a centrifugal extractor in counter-current flow with a mixture consisting of 150 kg./hour of dichloro methane and 50 kg./hour of trichloro fluoro methane within 60 seconds. During the extraction the temperature of the enzyme phase is increased to about 50° C. The solvent mixture is continuously recovered from the resulting fat-solvent phase by re-distillation and is recycled into the extraction process. The defattened enzyme phase is cooled in a heat exchanger to about 5° C. and is then evaporated in a short time evaporator (flash evaporator) at 40° C. and under a vacuum of 150 mm. Hg to a dry content of about 25%. The time of contact of the product with the heating medium is about 1 second. The resulting concentrate is cooled in a heat exchanger to about 5° C. and is then dried in a spray dried by means of filtered dry air. The yield of pancreatin amounts to about 5 kg./hour. The resulting product has the following properties:

Amylase Activity: 42,000 FIP* units per gram.
Lipase Activity: 58,000 FIP units per gram.
Protease Activity: 2,800 FIP units per gram.
Water content: 2.0%.
Fat content: 0.6%.
Bulk weight: 510 g. per liter.
Particle size:
30 – 50 $\mu$m: 80%.
10 – 30 $\mu$m: 10%.
smaller than 10 $\mu$m: 10%.
Germ count: $2 \times 10^3$ germs per gram.
Differentiation of germs: Only the apathogenic spore formers which are present in the starting material are found in the final product. Undesired germs could not be detected in the final product on testing in accordance with the specification of U.S. Pharmacopeia XVIIIth Revision.

* Determined according to the provisions of the Federation Internationale Pharmaceutique (cf: Hennrich, "Bestimmung von Pankreatin", *Pharm. Ind.*, vol. 31, p. 228 (1969).

EXAMPLE 2

30 kg./hour of deep-frozen pancreas glands (frozen at a temperature of −40° C.) are finely comminuted and ground in a continuously operating milling device in several steps. The fine powder of a temperature of −20° C. obtained thereby is mixed in a kneader mixer first with 15 kg./hour of a mixture of 7.5 kg. of trichloro methane and 7.5 kg. of trichloro trifluoro ethane, said mixture being at a temperature of 20° C., and thereafter with 60 kg./hour of water also of a temperature of 20° C. Thereupon the resulting paste is heated in a heat exchanger to 15° C. and is extracted therefrom in a centrifugal extractor below 30° C. in countercurrent flow with a mixture of 500 kg./hour of trichloro methane and 500 kg./hour of trichloro trifluoro ethane within 60 seconds. During said extraction the temperature of the enzyme phase is increased to a temperature not substantially exceeding 40° C. The solvent mixture is continuously recovered by redistillation from the resulting fat-solvent phase and is recycled into the extraction process. The defattened enzyme phase is cooled in a heat exchanger to about 5° C. and is then concentrated by evaporation in a short time evaporator (flash evaporator) at a temperature of 40°–50° C. and at a pressure of 150–230 mm. Hg to a dry content of 18%. The time of contact of the product with the heating medium amounts to about 3 seconds. The resulting concentrate is continuously freeze-dried. The yield of pancreatin amounts to 5.9 kg./hour. The resulting product has the following properties:

Amylast activity: 44,500 FIP units per gram.
Lipase activity: 57,200 FIP units per gram.
Protease activity: 2,500 FIP units per gram.
Water content: 1.5%.
Fat content: 1.1%.
Bulk weight: 500 g. per liter.
Particle size:
30 – 50 $\mu$m: 80%.
10 – 30 $\mu$m: 10%.
Smaller than 10 $\mu$m: 10%.
Germ count: $4 \times 10^3$ germs per gram.

Germ differentiation: Only the apathogenic spore forming microorganisms which are present in the starting material are found in the final product. Germs which according to the specification of U.S. Pharmacopeia XVIIIth Revision are undesired could not be detected in the final product.

What is claimed is:

1. A process of producing pancreatin of a high amylolytic, lipolytic, and proteolytic activity, said pancreatin having a low germ content and being substantially free of fibrous tissue material, comprising the steps of:
   a. contacting frozen, finely comminuted pancreas glands with a mixture of liquid chlorinated hydrocarbon and of a liquid fluoro-chloro-carbon, wherein the ratio of chlorinated hydrocarbon to fluoro-chloro-carbon is between 1:0.05 and 1:2.0, for a period of time sufficient to remove the fat therefrom and to destroy the pathogenic germs;
   b. separating the fat-solvent phase from the enzyme phase;
   c. concentrating the enzyme phase; and
   d. drying the concentrated enzyme phase.

2. The process of claim 1, in which water is added in the defattening and germ-destroying treatment of step (a).

3. The process of claim 1, in which the treatment of step (a) with the mixture of halogenated hydrocarbons is carried out within a period of about 30 seconds and about 5 minutes.

4. The process of claim 3, in which step (a) is carried out at a temperature between about 30° C. and about 60° C.

5. The process of claim 1, in which the boiling point of the halogenated hydrocarbon used in step (a) is between about 20° C. and about 150° C.

6. The process of claim 1, in which the chlorinated hydrocarbons are selected from the group consisting of trichloro methane, dichloromethane, dichloroethane, trichloroethane and tetrachloroethane.

7. The process of claim 1, in which the fluorochlorocarbons are selected from the group consisting of trichloro fluoro methane, trichloro trifluoro ethane, tetrachloro difluoroethane and pentachloro monofluoro ethane.

8. The process according to claim 1, in which the proportion, by weight, of pancreas glands to halogenated hydrocarbons used in step (a) is between about 1:2 and about 1:50.

9. The process of claim 2, in which the proportion, by weight, of pancreas glands to water in step (a) is between about 1:0 to 1:10.

10. The process of claim 1, in which in step (c) concentration of the defattened enzyme phase is effected by heating said enzyme phase at a temperature not exceeding about 60° C. in a vacuum within a contact time not exceeding 5 seconds.

11. The process of claim 1, further comprising the step of cooling said solutions to a temperature between 0° C. and 8° C. each time following process steps which are carried out at an increased temperature.

12. Pancreatin of a bulk weight between about 500 g. per liter and about 700 g. per liter and a mean particle diameter between about 30 $\mu$m. and about 50 $\mu$m., said pancreatin being substantially free of fibrous tissue material, being substantially free of pathogenic germs, having a low content of apathogenic germs, having a high enzymatic activity, and being readily flowable, said pancreatin being produced by the process of claim 1.

13. The process of claim 1, wherein the process is carried out on a continuous basis.

* * * * *